United States Patent
Aouak et al.

(10) Patent No.: US 12,269,787 B1
(45) Date of Patent: Apr. 8, 2025

(54) METHOD TO SELECTIVELY PRODUCE BENZALANILINE FROM A SCHIFF-BASE REACTION INVOLVING ANILINE AND BENZALDEHYDE

(71) Applicant: KING SAUD UNIVERSITY, Riyadh (SA)

(72) Inventors: Taieb Aouak, Riyadh (SA); Ahmad Almalki, Riyadh (SA); Waseem Sharaf Saeed, Riyadh (SA); Wafa Nazal Alharbi, Riyadh (SA); Abdel-Basit Al-Odayni, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/668,526

(22) Filed: May 20, 2024

(51) Int. Cl.
*C07C 209/78* (2006.01)
*C07C 209/86* (2006.01)

(52) U.S. Cl.
CPC .......... *C07C 209/78* (2013.01); *C07C 209/86* (2013.01)

(58) Field of Classification Search
None
See application file for complete search history.

(56) References Cited

U.S. PATENT DOCUMENTS

2017/0043302 A1  2/2017  Fedkiw et al.

FOREIGN PATENT DOCUMENTS

| CN | 101518719 A | 9/2009 | |
|---|---|---|---|
| EP | 0349204 A1 | 1/1990 | |
| JP | 2008031072 | * 2/2008 | .......... C07C 249/02 |
| WO | 2009/106002 A1 | 9/2009 | |

OTHER PUBLICATIONS

Verma et al., Scientific Reports (2022), vol. 12, Issue 1, p. 9636 (12 pages).*
Bigelow et al., "Benzalaniline," Organic Syntheses, Coll, vol. 1. p. 80 (1941, vol. 8, p. 22 (1928)).
Lau et al., "Zeolite membrane microreactors and their performance," Studies in surface science and catalysis, vol. 170. Elsevier, 2007, pp. 1460-1465.
Lau et al., "Knoevenagel condensation reaction between benzaldehyde and ethyl acetoacetate in microreactor and membrane microreactor," Microporous and Mesoporous Materials, vol. 115, Issues1-2, Oct. 2008: pp. 156-163.
"Elementary Work on Schiff Bases"; The art and science of amateur experimentalism, published online on Jan. 3, 2017.
Okuo et al., "Synthesis and Characterization of N-Benzylidene Aniline Ligand for Spectrophotometric Determination of Nickel." Chemistry and Materials Research, 2019, vol. 11, pp. 25-40.

* cited by examiner

Primary Examiner — Brian J Davis
(74) Attorney, Agent, or Firm — Nath, Goldberg & Meyer; Joshua B. Goldberg

(57) ABSTRACT

A method of making benzalaniline, the method comprising: providing benzaldehyde and aniline; performing a condensation reaction using a solvent; extracting water from the condensation reaction using a pervaporation system, wherein a poly(vinyl alcohol) PVA membrane is in the pervaporation system; and obtaining benzalaniline.

19 Claims, 2 Drawing Sheets

METHOD TO SELECTIVELY PRODUCE BENZALANILINE FROM A SCHIFF-BASE REACTION INVOLVING ANILINE AND BENZALDEHYDE

BACKGROUND

1. Field

The present disclosure relates to a method of producing benzalaniline, and more particularly, a method for producing benzalaniline using a Schiff-base reaction.

2. Description of the Related Art

The art of chemistry has always been a vehicle for the development of an active pharmaceutical compound. N-benzylideneanilines (cis and trans) of formula $C_6H_5CH=NC_6H_5$ are two isomere molecules which constitute one of these compounds and belongs to an important family of biologically active molecules. N-Benzylidèneaniline also called "Imines, Anils, Azomethines due to the presence of a C=N bond, in certain biological reactions prompted researchers to design different derivatives of this molecule having active antituberculosis (Emriye, A. Y. "Synthesis and Characterization of Schiff Base 1-Amino-4-methylpiperazine Derivatives." Celal Bayar Üniversitesi Fen Bilimleri Dergisi 12.3 (2016): 375-392.), antibacterial substituents (Reddy K. K., Rao S., Sreedhar R. B., Synthesis and Characterization and Biological Activities of Hydrazones, International Journal of Innovative Research in Science, Engineering and Technology, 2015; Vol. 4, Issue 1, 18944-18952), antifungal (Zoubi W. A., Biological Activities of Schiff Bases and Their Complexes: A Review of Recent Works, International Journal of Organic Chemistry, 2013; 3, 73-95.), anticancer (Arulmurugan S., Kavitha H. P. and Venkatraman B. R., Biological Activities of Schiff Base and its Complexes: A Review, Vol. 3, Rasayan J. Chem. 2010; No. 3, 385-410.), anti-inflammatory (Nichols C. J., Automated Combinatorial Chemistry in the Organic Chemistry Majors Laboratory, Journal of Chemical Education, 2010; Vol. 87, No. 1, 87-90.), antioxidant, and tyrosinase inhibitor (Koçyiğit-Kaymakçloğlu B., Elçin O., Seda U., Fatma K., Nathaly S., Sevim R., Dimoglo A. Synthesis and characterization of novel hydrazide hydrazones and the study of their structure-antituberculosis activity, European Journal of Medicinal Chemistry, 2006; 41, 1253-1261).

Bacterial infection remains a significant threat to human life due to its increasing resistance to conventional antibiotics, which is a growing public health concern. As a result, there is a critical need to create new antimicrobial agents with activity against potent anti-drug-resistant microorganisms.

In 1864, Hugo Schiff was the first to publish a work on the synthesis of imines and described the procedures for preparing many imine derivatives. This researcher published the standard synthesis which includes the condensation of amines with aldehydes and ketones under azeotropic condensation (H. Schiff, "Mittheilungen aus dem Universitätslaboratorium in Pisa: eine neue Reihe organischer Basen," European Journal of Organic Chemistry, vol. 131, no. 1, pp. 118-119, 1864.). This type of reaction, like that of esterification, is equilibrated in which the presence of water with the imine produced reproduces the reactants again. To orient the reaction process towards the selective production of imines, the water obtained as a by-product must be selectively removed.

Indeed, different techniques were reported in the literature to reach this goal, including solvent-free, microwave, ultrasound, water suspension medium, liquid crystals, and molecular sieves methods. For example, Westheimer et al. used the molecular sieves, but the results obtained lacked selectivity. F. Westheimer and K. Taguchi, "Catalysis by molecular sieves in the preparation of ketimines and enamines," The Journal of Organic Chemistry, vol. 36, no. 11, pp. 1570-1572, 1971.

In 1990, Gary-Look et al. investigated the removal of water from the Schiff-base reaction using tetra-methylorthosilicate and tri-methylorthoformate as dehydrating agents. C. Look, M. M. Murphy, D. A. Campbell, and M. A. Gallop, "Trimethylorthoformate: a mild and effective dehydrating reagent for solution and solid phase imine formation," Tetrahedron letters, vol. 36, no. 17, pp. 2937-2940, 1995. In 2004, Chakraborti et al. confirmed the evidence of this procedure and revealed that the increased efficacy was related to the strength of nucleophilic amines and the highly electrophilic carbonyl group compounds. A. K. Chakraborti, S. Bhagat, S. Rudrawar, "Magnesium perchlorate as an efficient catalyst for the synthesis of imines and phenylhydrazones," Tetrahedron Lett, 45 (41) (2004), pp. 7641-7644. These authors suggested activating the carbonyl group and catalyzing the nucleophilic amines by using Lewis acids, after removing water.

Recently, many new methods have been used to extract water resulting from Shiff-base reactions, such as microwave irradiation, free solvent with clay (CaO), water suspension medium, molecular sieves, infrared irradiation and silica with ultrasound irradiation. The results obtained revealed high performance only for certain components. F. Westheimer and K. Taguchi; R. S. Varma, R. Dahiya, and S. Kumar, "Clay catalyzed synthesis of imines and enamines under solvent-free conditions using microwave irradiation," Tetrahedron letters, vol. 38, no. 12, pp. 2039-2042, 1997; K. P. Guzen, A. S. Guarezemini, A. T. Orfao, R. Cella, C. M. Pereira, and H. A. Stefani, "Eco-friendly synthesis of imines by ultrasound irradiation," Tetrahedron letters, vol. 48, no. 10, pp. 1845-1848, 2007.

It was further revealed that microwave irradiation has several advantages, such as less solvent consumption, high efficiency, and shorter time period.

Thus, new methods for forming molecules having desired therapeutic activities and solving the aforementioned problems are desired.

SUMMARY

The present subject matter focuses on the use of the technique of pervaporation in the selective extraction of water as it is formed in order to increase the yield of benzalaniline from the condensation reaction involving aniline and benzaldehyde as reactants and ethanol and n-hexane as solvents. To achieve this goal, a series of poly (vinylalcohol) membranes of different thicknesses was prepared and crosslinked by a thermal route. These membranes are characterized by different techniques, testing its competence in separating water from the mixture containing aniline, benzaldehyde, benzalaniline, water and ethanol or n-hexane.

In an embodiment, the present subject matter relates to a method of making benzalaniline, the method comprising: providing benzaldehyde and aniline; performing a condensation reaction using a solvent; extracting water from the condensation reaction using a pervaporation system, wherein a poly(vinyl alcohol) PVA membrane is in the pervaporation system; and obtaining benzalaniline.

In another embodiment, the present subject matter relates to a method of making benzalaniline, the method comprising: providing a solution of benzaldehyde and aniline; adding n-hexane to the solution to obtain a reaction mixture; carrying out condensation reaction on the reaction mixture; extracting water from the reaction mixture using a pervaporation system, wherein a poly(vinyl alcohol) PVA membrane is in the pervaporation system; and obtaining benzalaniline.

These and other features of the present subject matter will become readily apparent upon further review of the following specification.

DETAILED DESCRIPTION OF THE PREFERRED EMBODIMENTS

Figure 1:
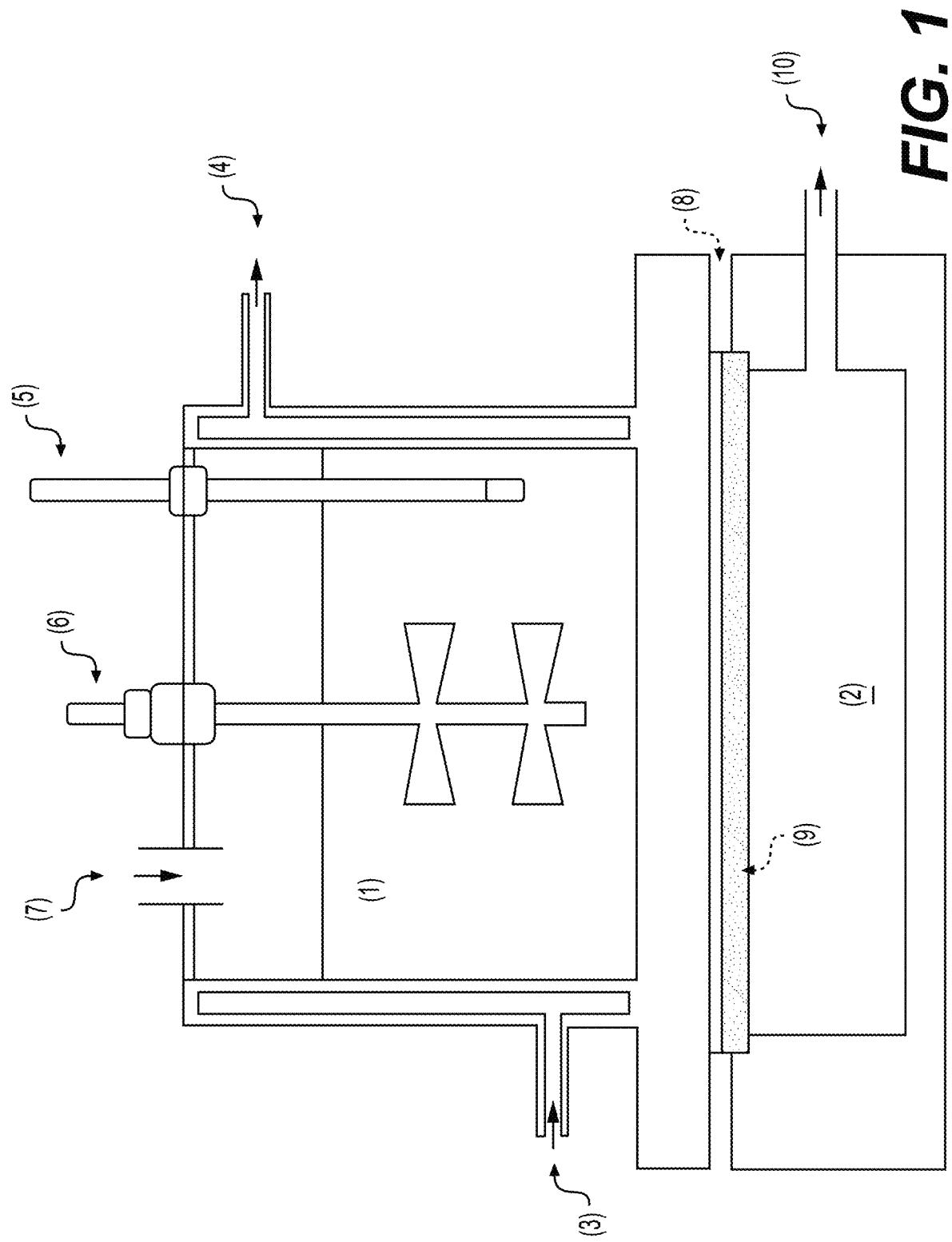
FIG. 1 illustrates an embodiment of a pervaporation apparatus used in an exemplary method of selectively producing benzalaniline.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter focuses on the use of the technique of pervaporation in the selective extraction of water as it is formed, in order to increase the yield of benzalaniline from the condensation reaction involving aniline and benzaldehyde as reactants and ethanol and n-hexane as solvents. To achieve this goal, a series of poly (vinylalcohol) (PVA) membranes of different thicknesses was prepared and crosslinked by a thermal route. These membranes were characterized by different techniques, testing its competence in separating water from the mixture containing aniline, benzaldehyde, benzalaniline, water and ethanol or n-hexane. Different parameters that may affect yield and selectivity of the principal product such as membrane thickness and crosslinking density, temperature and solvent were investigated.

Pervaporation is an eco-friendly and economical membrane technique used in the selective extraction of volatile compounds in small amounts. The key element of this technique is the correct choice of membrane. In the separation of water from hydro-organic mixtures such as alcohols, carboxylic acids and amines, the works carried out so far indicate that the most competitive membranes for this purpose are made from poly (vinyl alcohol)(PVA). Different parameters influencing the results of the reaction process and the results obtained are high selectivity to the removal of water from the reaction mixture. Moreover, the conversion of propanonic acid was enhanced by enhancing the catalyst amount, molar ratio of acid to alcohol, reaction temperature, and ratio of membrane area to initial reaction volume.

The present subject matter focuses on the use of pervaporation in the selective extraction of water as it is formed in order to increase the yield of benzalaniline from the condensation reaction involving aniline and benzaldehyde as reactants and ethanol and n-hexane as solvents. To achieve this goal, a series of poly (vinylalcohol) membranes of different thicknesses was prepared and crosslinked by a thermal route. These membranes are characterized by different techniques, testing its competence in separating water from the mixture containing aniline, benzaldehyde, benzalaniline, water and ethanol or n-hexane. Different parameters that may affect the yield and selectivity of the principal product, such as membrane thickness and crosslinking density, temperature and solvent have also been investigated.

In an embodiment, the present subject matter relates to a method of making benzalaniline, comprising: providing benzaldehyde and aniline; performing a condensation reaction using a solvent; extracting water from the condensation reaction using a pervaporation system, wherein a poly(vinyl alcohol) PVA membrane is in the pervaporation system; and obtaining benzalaniline.

In an embodiment, an amount of benzaldehyde may be between about 12.38 wt % to about 12.79 weight %.

In a further embodiment, the amount of aniline may be between about 12.17 wt % to about 12.92 weight %.

In another embodiment, the solvent may be n-hexane. The concentration of n-hexane may be between 2.00 mol·L$^{-1}$ and 4.00 mol·L$^{-1}$ In a further embodiment, the condensation reaction may occur for at least about two hours.

In an additional embodiment, the PVA membrane may have a thickness of about m. The PVA membrane may be crosslinked at temperatures between about 110° C. to about 130° C. The PVA membrane may be crosslinked at 110° C., 120° C., and 130° C. The PVA membrane may be crosslinked at a pressure of 50 bar for at least about 1 hour.

In an embodiment, the condensation reaction may occur at 24° C.

In another embodiment, the benzalaniline is obtained at about a 99% yield. In various embodiments, the benzalaniline is obtained at 99.84% yield to a 99.98% yield, In an embodiment, the present subject matter may includes a method of making benzalaniline, the method comprising: providing a solution of benzaldehyde and aniline; adding a solvent to the solution to obtain a reaction mixture; carrying out a condensation reaction on the reaction mixture; extracting water from the reaction mixture using a pervaporation system, wherein a poly(vinyl alcohol) PVA membrane is in the pervaporation system; and obtaining benzalaniline.

In an embodiment, an amount of benzaldehyde may be between about 12.38 wt % to about 12.79 weight %.

In a further embodiment, the amount of aniline may be between about 12.17 wt % to about 12.92 weight %.

In another embodiment, the solvent may be n-hexane. The concentration of n-hexane may be between 2.00 mol·L$^{-1}$ and 4.00 mol·L$^{-1}$ In a further embodiment, the condensation reaction may occur for at least about two hours.

In an additional embodiment, the PVA membrane may have a thickness of about m. The PVA membrane may be crosslinked at temperatures between about 110° C. to about 130° C. The PVA membrane may be crosslinked at 110° C., 120° C., and 130° C. The PVA membrane may be crosslinked at a pressure of 50 bar for at least about 1 hour.

In an embodiment, the condensation reaction may occur at either 25° C. or 50° C. (Table 2).

Said another way, the present subject matter relates to a method to obtain better yields from the condensation reaction of Schiff's base between aniline and benzaldehyde, leading to the formation of benzalaniline following the reaction of Scheme 1:

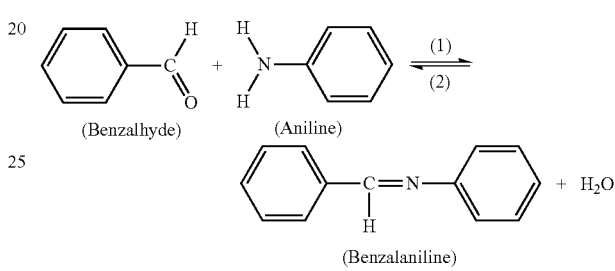

Referring to FIG. 1, the elements of the pervaporation cell include a reaction mixture 1; a permeate (principally water) 2; a liquid thermostat (input) 3; a liquid thermostat (output) 4; a thermometer 5; a mechanical stirrer 6; a feed input 7; a porous stainless steel support 8, a membrane 9; and a permeate output 10.

Figure 2:
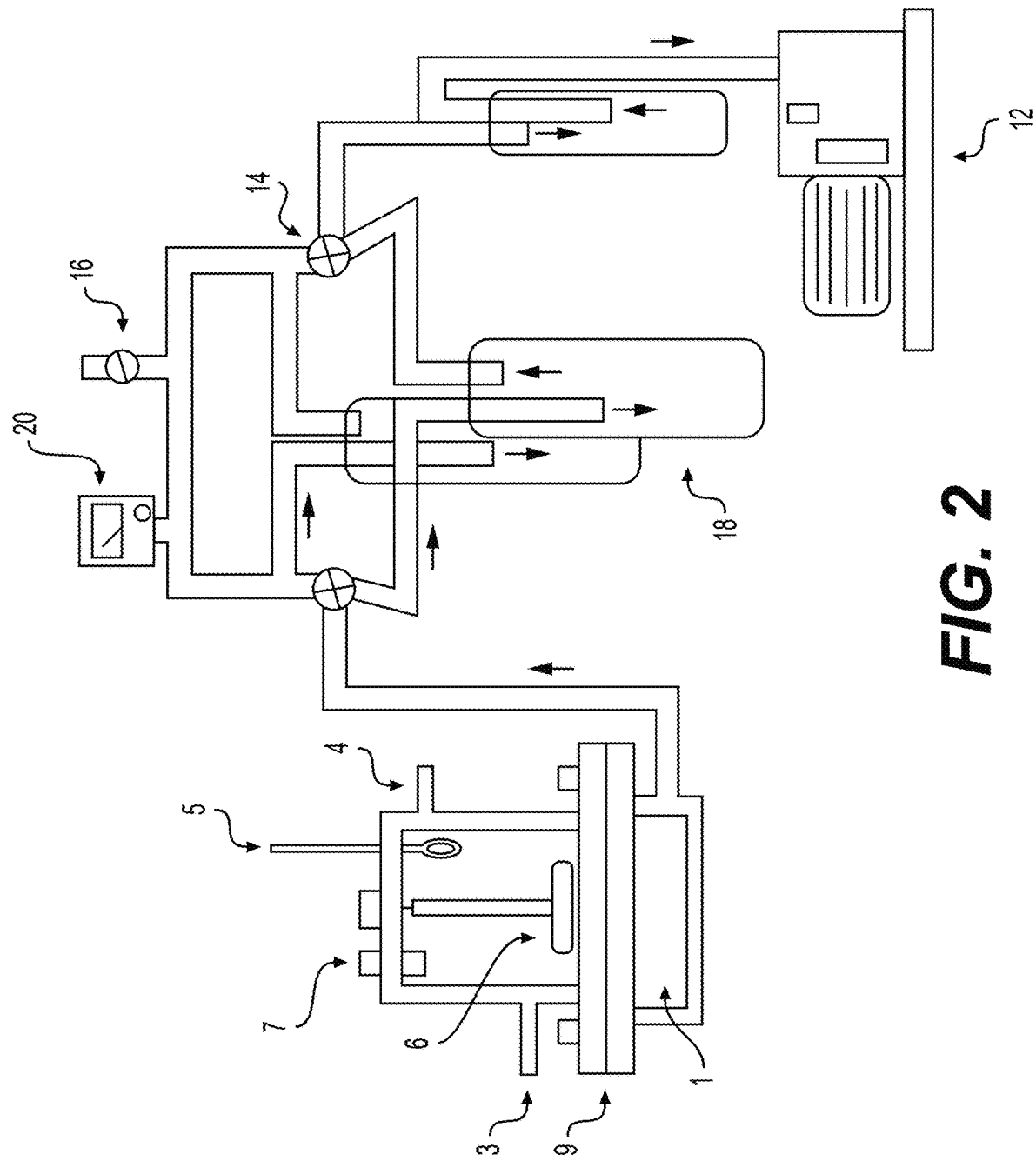
FIG. 2 illustrates an embodiment of a pervaporation cell used in an exemplary method of selectively producing benzalaniline.

Referring to FIG. 2, the pervaporation apparatus illustrated includes a vacuum pump 12, a three-way Rota Float valve 14, two-way Rota Float valve 16, a cooled trap 18, a Pirani gauge 20, and a cell similar to that in FIG. 1.

The following examples relate to various methods of manufacturing the specific compounds and application of the same, as described herein. All compound numbers expressed herein are with reference to the synthetic pathway figures shown above.

EXAMPLES

Materials

Aniline (99.0% purity) was provided from CDH Fine chemicals (India). Benzaldehyde (Lobachemi, India, purity 99%) and n-hexane (97%) and ethanol (purity 99.9%) were purchased from BDH Chemicals (United States). Poly (vinyl alcohol) (PVA)($\overline{M}n=1.05 \cdot 10^6$ g·mol$^{-1}$, 98% hydrolyzed) was provided from Aldrich (Germany). All chemicals were used without further purification.

Example 1

Membrane Preparation

Different membranes with different thicknesses were prepared from poly(vinyl alcohol)(PVA), crosslinked under high pressure and at different temperatures. In a 1000 mL-flask, 50 g of PVA was dissolved in 500 mL of distilled water, under continuous stirring at 80° C. for 8 hours. The prepared solution was cooled down at room temperature and filtrated to avoid any impurities, such as dust and undissolved PVA microgel. To control the uniformity of membrane thickness, the filtrated solution was poured onto a flat-surface Teflon mold (20 cm²×20 cm²), held horizontally using a level, then left to dry at 40° C. for 8 hours and under vacuum for 5 hours. The dried membranes obtained were then thermally crosslinked using a press machine COLLIN-Platen Press P300 P/M PMAX, Hydraulic 250 bar, 300° C. according to the mechanism presented in Scheme 2.

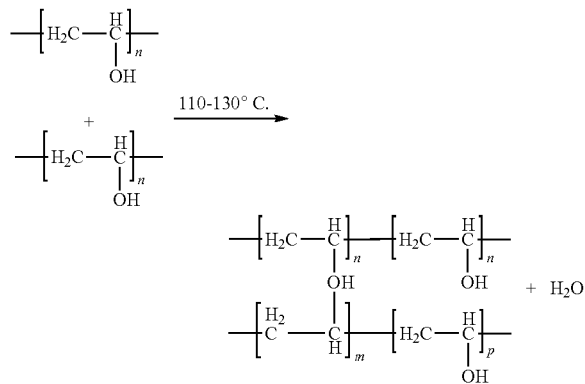

Scheme 2

A series of PVA membranes having different thickness was prepared by this method by varying the concentration of PVA solution. The crosslinking degree of each membrane was controlled on the time-temperature at constant pressure of 50 bar. Twelve PVA membranes with different thicknesses and crosslinking degrees were prepared by heating at 110° C., 120° C. and 130° C., under a pressure of 50 bar for 1.0 hour. The preparation conditions and their thicknesses are summarized in Table 1. It should be understood that a press machine is advantageous for achieving a flat film and protecting the PVA membrane from oxygen to avoid PVA oxidation at these temperatures.

TABLE 1

Table 1
Preparation conditions of
crosslinked PVA membranes with different thickness

| PVA membranes | PVA concentration (g · L⁻¹) | Temperature (° C.) | Thickness |
|---|---|---|---|
| NC-PVA-20 | 34.0 | 25 | 20 |
| NC-PVA-30 | 54.0 | | 30 |
| NC-PVA-40 | 70.0 | | 40 |
| C-PVA-110-20 | 34.0 | 110 | 20 |
| C-PVA-110-30 | 54.0 | | 30 |
| C-PVA-110-40 | 70.0 | | 40 |
| C-PVA-120-20 | 34.0 | 120 | 20 |
| C-PVA-120-30 | 54.0 | | 30 |
| C-PVA-120-40 | 70.0 | | 40 |
| C-PVA-130-20 | 34.0 | 130 | 20 |
| C-PVA-130-30 | 54.0 | | 30 |
| C-PVA-130-40 | 70.0 | | 40 |

Example 2

Pervaporation Process

To achieve this goal, the reaction was carried out in a pervaporation cell, as illustrated in FIG. 1, to selectively extract water produced as a by-product in order to orient the reaction towards the selective production of benzalaniline (direction 1 of Scheme 1). Referring again to FIG. 1, the elements of the pervaporation cell include a reaction mixture 1; a permeate (principally water) 2; a liquid thermostat (input) 3; a liquid thermostat (output) 4; a thermometer 5; a mechanical stirrer 6; a feed input 7; a porous stainless steel support 8, a membrane 9; and a permeate output 10.

The condensation reaction was carried out in two different solvents, ethanol (polar solvent) and n-hexane (non-polar solvent) (Table 2) and at different temperatures (25° C. and 50° C.) using a pervaporation apparatus, similar to that of FIG. 2. Referring to FIG. 2, the pervaporation apparatus illustrated includes a vacuum pump 12, a three-way Rota Float valve 14, two-way Rota Float valve 16, a cooled trap 18, a Pirani gauge 20, and a cell similar to that in FIG. 1. To demonstrate the performance of the process of the invention, a reference reaction was carried out involving benzaldehyde and aniline under the same conditions but without being assisted by pervaporation.

TABLE 2

Table 2
Conditions of the Schiff-base reaction
occurred between benzaldehyde and aniline

| Solvent | Temperature (° C.) | Reactants (wt %) | | Solvent (mol · l⁻¹) |
|---|---|---|---|---|
| | | Aniline | Benzaldehyde | |
| Ethanol | 25 | 12.87 | 12.43 | 1.00 |
| | 25 | 12.92 | 12.67 | 2.00 |
| | 25 | 12.17 | 12.38 | 4.00 |
| | 50 | 12.39 | 12.51 | 4.00 |
| Hexane | 25 | 12.67 | 12.79 | 2.00 |
| | 25 | 12.56 | 12.74 | 4.00 |
| | 50 | 12.80 | 12.71 | 4.00 |

Example 3

Results

The results obtained were very satisfactory in terms of yield and purity. Indeed, by varying the thickness of the membrane, the degree of crosslinking, the polarity of the solvent, and the temperature of the reaction-pervaporation system, it was revealed that between 99.84 and 99.98 wt % of benzalaniline yield are obtained in the n-hexane for a period of 2 hours under certain conditions instead of 72.12 and 70.05 wt % when these same reactions occurred under the same conditions and not assisted by pervaporation.

It is to be understood that the method of making benzalaniline are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making benzalaniline, the method comprising:
providing an amount of benzaldehyde and an amount of aniline;
performing a condensation reaction using a solvent;
extracting water from the condensation reaction using a pervaporation system, wherein a poly(vinyl alcohol) PVA membrane is in the pervaporation system; and
obtaining benzalaniline;
wherein the solvent is n-hexane.

2. The method of claim 1, wherein an amount of benzaldehyde is between about 12.38 wt % of the total weight of the benzaldehyde, the aniline, and the solvent to about 12.79 wt % of the total weight of the benzaldehyde, the aniline, and the solvent.

3. The method of claim 1, wherein the amount of aniline is between about 12.17 wt % of the total weight of the benzaldehyde, the aniline, and the solvent to about 12.92 wt % of the total weight of the benzaldehyde, the aniline, and the solvent.

4. The method of claim 1, wherein the concentration of n-hexane is between 2.00 mol·L$^{-1}$ and 4.00 mol·L$^{-1}$.

5. The method of claim 1, wherein the condensation reaction occurs for at least about 2 hours.

6. The method of claim 1, wherein the PVA membrane has a thickness of about 30 μm.

7. The method of claim 1, wherein the PVA membrane is crosslinked at temperatures between about 110° C. to about 130° C.

8. The method of claim 1, wherein the PVA membrane is crosslinked at a pressure of 50 bar for at least about 1 hour.

9. The method of claim 1, wherein the condensation reaction occurs at 24° C.

10. The method of claim 1, wherein the benzalaniline is obtained at about a 99% yield.

11. A method of making benzalaniline, the method comprising:
providing a solution of benzaldehyde and aniline;
adding n-hexane to the solution to obtain a reaction mixture;
carrying out a condensation reaction on the reaction mixture;
extracting water from the reaction mixture using a pervaporation system, wherein a poly(vinyl alcohol) PVA membrane is in the pervaporation system; and
obtaining benzalaniline.

12. The method of claim 11, wherein an amount of benzaldehyde is between about 12.38 wt % of the total weight of the benzaldehyde, the aniline, and the solvent to about 12.79 wt % of the total weight of the benzaldehyde, the aniline, and the solvent.

13. The method of claim 11, wherein the amount of aniline is between about 12.17 wt % of the total weight of the benzaldehyde, the aniline, and the solvent to about 12.92 wt % of the total weight of the benzaldehyde, the aniline, and the solvent.

14. The method of claim 11, wherein the condensation reaction occurs for at least about 2 hours.

15. The method of claim 11, wherein the PVA membrane has a thickness of about 30 μm.

16. The method of claim 11, wherein the PVA membrane is crosslinked at temperatures between about 110° C. to about 130° C.

17. The method of claim 11, wherein the PVA membrane is crosslinked at a pressure of 50 bar for at least about 1 hour.

18. The method of claim 11, wherein the condensation reaction occurs at 24° C.

19. The method of claim 11, wherein the benzalaniline is obtained at about a 99% yield.

* * * * *